United States Patent [19]
Mihara et al.

[11] 3,999,947
[45] Dec. 28, 1976

[54] REDUCING GAS SENSOR AND A METHOD OF PRODUCING THE SAME

[75] Inventors: Toshihiro Mihara; Masatake Ayusawa, both of Hirakata; Keiji Matsumoto, Ibaragi; Kunio Sato, Neyagawa; Yoshio Iida, Suite, all of Japan

[73] Assignee: Matsushita Electric Industrial Co., Ltd., Japan

[22] Filed: Oct. 1, 1975

[21] Appl. No.: 618,680

[30] Foreign Application Priority Data

Oct. 11, 1974 Japan .................... 49-116965
Oct. 11, 1974 Japan .................... 49-116966
Oct. 29, 1974 Japan .................... 49-125006

[52] U.S. Cl. ............... 23/254 E; 73/23; 324/71 SN; 338/34
[51] Int. Cl.² ............... G01N 27/00; G01N 33/00
[58] Field of Search ......... 23/232 E, 254 E, 255 E; 340/237 R, 237 S; 73/23, 27 R; 324/71 SN; 338/13, 22 SD, 34; 200/61.03; 29/570, 576, 589; 252/519

[56] References Cited
UNITED STATES PATENTS

| 3,382,174 | 5/1968 | Hund | 423/634 X |
| 3,695,848 | 10/1972 | Taguchi | 23/254 E |
| 3,843,773 | 10/1974 | Pingaud | 423/634 |

*Primary Examiner*—Joseph Scovronek
*Attorney, Agent, or Firm*—Wenderoth, Lind & Ponack

[57] ABSTRACT

This invention provides a reducing gas sensor which has a gas sensitive element of γ-ferric oxide ($\gamma$-$Fe_2O_3$), a pair of electrodes and a heater element. The γ-ferric oxide is in the form of a thin film, a plate or a thin surface layer on a sintered plate of α-ferric oxide. This invention also provides a method of producing the reducing gas sensor, which includes the steps of firing $\gamma$-$Fe_2O_3$, γ-FeOOH or $Fe_3O_4$ powder on a substrate and applying thereto a pair of electrodes and a heater element; or sintering alpha-ferric oxide ($\alpha$-$Fe_2O_3$) and reducing it to magnetite and oxidizing it at the surface thereof to γ-ferric oxide as a gas sensitive element. The sensitivity ($R_A/R_G$) of the gas sensitive element of γ-ferric oxide is 10 to 130° at 270° C in an atmosphere containing 0.1 to 1 percent by volume propane gas, and the reducing gas sensor has high sensitivity and stability.

12 Claims, 10 Drawing Figures

REDUCING GAS SENSOR AND A METHOD OF PRODUCING THE SAME

This invention relates to a reducing gas sensor comprising a gas sensitive element, a pair of electrodes applied to the sensitive element and a heater element, and also relates to a method of producing the same.

Several materials are known to be sensitive to reducing gases and have been used in the reducing gas sensor as sensitive elements. They undergo a change in properties (e.g. color, electrical resistance, etc.) upon coming in contact with an atmosphere containing a reducing gas.

Among the known gas sensitive materials used in a reducing gas sensor, palladium compounds undergo an irreversible change in color upon coming in contact with an atmosphere containing carbon monoxide gas. The color change of palladium compounds applied to a transparent base can be detected by a photo-electric cell. The gas sensor using such palladium compounds has disadvantages in that the gas sensitive element undergoes an irreversible change in color, and so it cannot be used repeatedly and in that it must be used immediately after preparation, because the color change occurs even with a small amount of CO gas in the air during storage.

Another known gas sensitive material is a resistor of platinum wire. A reducing gas in air is oxidized in the presence of a catalyst and increases the temperature of the surroundings. The electrical resistance of a platinum wire with an oxidizing catalyst of platinum black is increased upon coming upon contact with the reducing gases, because of an increase of the temperature of the wire. This type of reducing gas sensor has disadvantages in that the sensitivity is fairly small and the gas sensitive element is expensive. Also, the temperature of the sensitive element must be precisely controlled in temperature.

Recently several metal oxide semiconductors have been used as gas sensitive elements in a reducing gas sensor. The metal oxides of N-type semiconductors undergo a rapid decrease in electrical resistance upon coming in contact with a reducing gas. The change of electrical resistance of the semiconductors is reversible. A reducing gas sensor using such semiconductors has a simple structure and has high sensitivity.

One of these semiconductors is stannic dioxide disclosed by U.S. Pat. No. 3,695,848. The stannic dioxide gas sensitive element has high sensitivity but has several disadvantages such as a large temperature dependence of the electrical resistance and a decrease of the sensitivity at an elevated temperature up to 300° C and also a short life time. Another of these known semiconductors is zinc oxide (ZnO) and/or cadmium oxide (CdO). The sensitivity of a sensitve element of (ZnO) or (CdO) is farily low. Still others of these semiconductors are titanium dioxide ($TiO_2$), ferric oxide ($Fe_2O_3$), alumina ($Al_2O_3$), tungsten trioxide ($WO_3$) and molybdenum trioxide ($MoO_3$). However, the change of the electrical resistivity of these materials exposed to an atmosphere containing a reducing gas can be scarcely observed, as taught by the Journal of Analytical Chemistry, 38 (8) 1069 (1966). Therefore, these materials have not been used as sensitive elements in a reducing gas sensor.

It is an object of this invention to provide a reducing gas sensor which has high sensitivity and stability during use.

It is another object of this invention to provide a method of producing a reducing gas sensor which has high sensitivity and stability during use.

These and other objects and features of this invention will be apparent upon consideration of the following description taken together with the accompanying drawings, in which.

Figure 1:
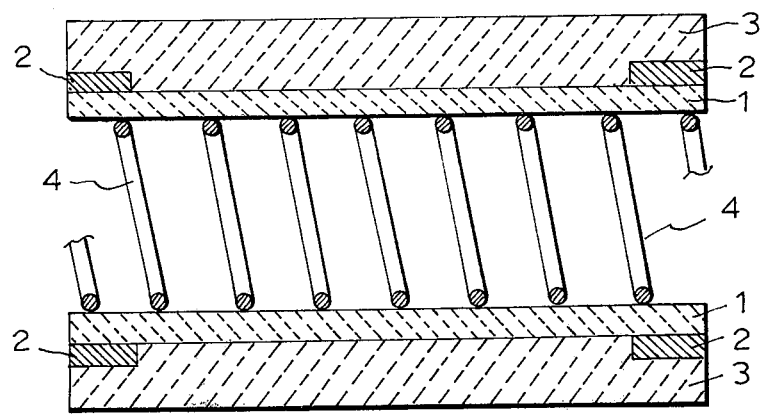
FIG. 1 is a cross-sectional view of an example of a reducing gas sensor contemplated by this invention.

According to this invention, the reducing gas sensor comprises a gas sensitive element composed mainly of γ-ferric oxide (γ-$Fe_2O_3$), a pair of electrodes applied to the sensitive element and a heater element for heating the gas sensitive element so that the gas sensitive element at an elevated temperature undergoes a rapid decrease in electrical resistance upon coming in contact with an atmosphere containing a reducing gas. According to the method of this invention, an iron oxide is fired at a temperature between 100° C and 600° C for 30 minutes to 5 hours in an oxidizing atmosphere to obtain a sintered γ-ferric oxide (γ-$Fe_2O_3$) as a gas sensitive element, a pair of electrodes are applied to the gas sensitive element and a heater element is placed near the gas sensitive element.

There are many types of crystal structure of ferric oxide ($Fe_2O_3$). They are alpha-ferric oxide (α-$Fe_2O_3$), beta-ferric oxide (β-$Fe_2O_3$), gamma-ferric oxide (γ-

$Fe_2O_3$), delta-ferric oxide ($\delta$-$Fe_2O_3$), epsilon-ferric oxide ($\epsilon$-$Fe_2O_3$) and eta-ferric oxide ($\eta$-$Fe_2$-$O_3$). Alpha-ferric oxide is mostly used as a raw material in various industries. Therefore, the unmodified expression "ferric oxide" usually means $\alpha$-ferric oxide ($\alpha$-$Fe_2O_3$), which has a corundum type of crystal structure. Beta, delta, epsilon and eta-ferric oxides have hardly ever been used in industry.

Gamma-ferric oxide ($\gamma$-$Fe_2O_3$) has been used as a magnetic recording media for a magnetic recording tape or disk. $\gamma$-$Fe_2O_3$ has a spinel type of crystal structure and it has been called maghemite, gamma hematite or gamma ferric oxide, but it has never been called merely hematite or ferric oxide, because it is quite different from $\alpha$-$Fe_2O_3$. One is magnetic, the other is non-magnetic.

In this invention, each of the various types of ferric oxides in powder form is mixed with water in a ball mill to a slurry which is a homogeneous mixture. The mixture is applied as a thin film on an insulator substrate e.g. of alumina and heated e.g. at 400° C e.g. for 1 hour in air. A pair of electrodes are applied to the thin film. The sensitivity of the iron oxide as a gas sensitive element of a reducing gas sensor is defined as the ratio of the electrical resistance in air to that in an atmosphere containing a reducing gas at an elevated temperature between 250° C and 350° C. The electrical resistances of the gas sensitive element are $R_A$ in air and $R_G$ in an atmosphere containing a reducing gas. The value of the ratio ($R_A/R_G$) indicates the sensitivity of the gas sensitive element. The electrical resistances are measured in air and in an atmosphere containing e.g. 1 volume percent of propane gas e.g. at 270° C. The sensitivity ($R_A/R_G$) of the $\gamma$-$Fe_2O_3$ is about 10 to about 130. On the other hand, the sensitivity of the $\alpha$-$Fe_2O_3$ is about 2 to about 5. Furthermore, the $\alpha$-$Fe_2O_3$ has an extremely high electrical resistivity. The sensitivities of the gas sensitive elements of other types of ferric oxides (e.g. $\beta$-$Fe_2O_3$, $\delta$-$Fe_2O_3$, $\epsilon$-$Fe_2O_3$ and $\eta$-$Fe_2O_3$) are about 1 to about 5. Extremely high values of sensitivity are observed in only $\gamma$-type ferric oxide.

The $\gamma$-ferric oxide as a gas sensitive element in a reducing gas sensor can have the form of a sintered body. The sintered body of $\gamma$-ferric oxide can be in the form of a thin film, a plate, a thin surface layer on sintered $\delta$-$Fe_2O_3$, etc. The sintered body of $\gamma$-ferric oxide is superior in mechanical strength and stability as a gas sensitive element.

A reducing gas sensor of this invention composed mainly of a $\gamma$-ferric oxide, preferably sintered, as a gas sensitive element is produced, in a generic way, by firing iron oxides at a temperature preferably between about 100° C and about 600° C in an oxidizing atmosphere, applying a pair of electrodes to the gas sensitive element and providing therewith a heater element.

In one specific method of this invention, a $\gamma$-ferric oxide in the form of a sintered body is produced by mixing $\gamma$-ferric oxide powder and water in a homogeneous mixture, applying the mixture to an insulator substrate to form a thin film of the mixture, and firing the thin film at a temperature preferably between about 350° C and about 600° C preferably for about 30 minutes to about 5 hours in an oxidizing atmosphere. When the thin film is fired at a temperature lower than about 350° C for a time shorter than about 30 minutes, the film is weak in mechanical strength, and when the thin film is fired at a temperature higher than about 600° C or for a time longer than about 5 hours, the sensitivity of the film as a gas sensitive element is low.

In another specific method of this invention, a sintered body of $\gamma$-ferric oxide is produced by mixing lepidocrocite ($\gamma$-FeOOH) powder and water in a homogeneous mixture, applying the mixture to an insulator substrate to form a thin film of the mixture and firing the film at a temperature preferably between about 150° C and about 600° C preferably for about 30 minutes to about 5 hours in an oxidizing atmosphere. When the film is fired at a temperature lower than about 150° C or for a time shorter than about 30 minutes, the film is weak in mechanical strength and when the thin film is fired at a temperature higher than about 600° C or for a time longer than about 5 hours, the sensitivity of the film as a gas sensitive element is low.

According to still another specific method of this invention, a sintered body of $\gamma$-ferric oxide is produced by using magnetite powder as a raw material, mixing the magnetite ($Fe_3O_4$) and water in a ball mill to prepare a homogeneous mixture in the form of a slurry, applying the mixture to an insulator substrate to form a thin film, and firing the thin film at a temperature preferably between about 100° C and about 600° C preferably for about 30 minutes to about 5 hours in an oxidizing atmosphere. When the film is fired at a temperature lower than about 100° C or for a time shorter than about 30 minutes, the electrical resistance of the film is low and unstable and when the film is fired at a temperature higher than about 600° C or for a time longer than about 5 hours, the electrical resistance is high and the sensitivity of the film is low.

According to a specific alternative method of this invention, a magnetite powder is pressed to produce a plate and prefired at a temperature preferably between about 600° C and about 1100° C preferably for about 30 minutes to about 10 hours in a non-oxidizing atmosphere and then fired at a temperature preferably between about 100° C and about 600° C in an oxidizing atmosphere preferably for about 30 minutes to about 5 hours. When the plate is prefired at a temperature lower than about 600° C or for a time shorter than about 30 minutes, the plate is weak in mechanical strength and when the plate is prefired at a temperature higher than about 1100° C or for a time longer than about 10 hours, the plate has a low sensitivity.

According to another specific alternative method of this invention, a sintered $\gamma$-ferric oxide is produced by using $\alpha$-ferric oxide powder as a raw material, mixing the $\alpha$-ferric oxide powder and polyvinyl alcohol solution into a mixture, applying the mixture onto an insulator substrate to form a thin film, prefiring the thin film at a temperature preferably between about 700° C and about 1300° C preferably for about 1 to about 10 hours in air to form a sintered film of $\alpha$-ferric oxide, firing the prefired film at a temperature preferably between about 200° C and about 450° C preferably for about 15 minutes to about 3 hours in hydrogen gas saturated with water vapor to form a thin film of magnetite ($Fe_3O_4$), and finally firing the thin film of the thus made magnetite at a temperature preferably between about 100° C and about 600° C preferably for about 1 to about 5 hours to form a sintered film of $\gamma$-ferric oxide. When the film is prefired at a temperature lower than about 700° C or for a time shorter than about 1 hour, the film is weak in mechanical strength, and when the film is prefired at a temperature higher than about 1300° C or for a time longer than about 10 hours, the film will not be completely transformed to magnetite, and γ-ferric oxide produced at a later stage after after-heat treatment will have a low sensitivity. When the film is fired, after the prefiring, at a temperature lower than about 200° C or for a time shorter than about 15 minutes, the film is not completely transformed to a film of magnetite, and when the prefired film is fired at a temperaure higher than about 450° C or for a time longer than about 3 hours, the resultant film has a low sensitivity.

According to still another specific alternative method of this invention, a sintered γ-ferric oxide is produced by pressing an α-ferric oxide powder to produce a plate, prefiring the plate at a temperature preferably between about 800° and about 1000° C preferably for about 1 to about 3 hours in an oxidizing atmosphere to form a sintered plate of α-ferric oxide, firing the prefired plate at a temperature preferably between about 200° C and about 450° C preferably for about 10 minutes to about 2 hours in hydrogen gas saturated with water vapor to form a sintered surface layer of magnetite ($Fe_3O_4$) on the sintered plate of α-ferric oxide, and finally firing the sintered plate of α-ferric oxide having the thin surface layer of magnetite thereon at a temperature preferably between about 100° C and about 600° C preferably for about 30 minutes to about 3 hours in an oxidizing atmosphere to transform the thin surface layer of magnetite to a thin surface layer of γ-ferric oxide on the sintered plate of α-ferric oxide. When the plate is prefired at a temperature lower than about 800° c or for a time shorter than about 1 hour, the plate is weak in mechanical strength, and when the plate is prefired at a temperature higher than about 1000° C or for a time longer than about 3 hours, the surface layer of the plate will not be transformed to magnetite, and γ-ferric oxide produced at a later state after after-heat treatment will have a low sensitivity. When the plate is fired, after the prefiring, at a temperature lower than about 200° C or for a time shorter than about 10 minutes, the surface layer of the plate is not completely transformed to a thin surface layer of magnetite ($Fe_3O_4$), and when the prefired plate is fired at a temperature higher than about 450° C or for a time longer than about 2 hours, the surface layer of the plate have a low sensitivity. When the plate of α-ferric oxide having the surface layer of magnetite thereon is fired at a temperature lower than about 100° C or for a time shorter than about 30 minutes, the surface layer of the sintered plate is not transformed to γ-ferric oxide, and when the plate is fired at a temperature higher than 600° C or for a time longer than about 3 hours, the surface layer of the sintered body have a low sensitivity.

A reducing gas sensor according to this invention has a markedly high sensitivity and stability.

This invention will be more readily understood with reference to the following Examples, but these Examples are intended to illustrate this invention only, and are not to be construed to limit thereby the scope of the invention.

EXAMPLE I

Five hundred grams of γ-ferric oxide powder which have an average particle size of 0.8 micron and one liter of distilled water were mixed in a ball mill for one hour to produce a homogeneous slurry. Referring to FIG. 1, the homogeneous slurry 3 was applied on a forsterite tube 1 which had an outer diameter of 5 mm, an inner diameter of 3 mm and a length of 15 mm. The forsterite tube had gold electrodes 2 2 mm in width deposited on both ends. The forsterite tube with the mixture as a film on the central portion thereof was dried at room temperaure and then fired at 350° C for an hour in air. The fired film of γ-$Fe_2O_3$ was 20 microns thick and was a gas sensitive element 3. A heater element 4 in the form of a coiled platinum wire 0.1 mm in diameter was placed in contact with the inner surface of the forsterite tube. The thus produced reducing gas sensor was placed in a measuring chamber in the form of a glass tube 40 mm in inner diameter and 100 mm in length. The chamber had an inlet and outlet for gas. A gas tank of air and a gas tank of air containing 1 percent by volume propane were connected to the inlet through a flow meter and a bulb. The platinum coil 4 in the forsterite tube was connected to an electrical transformer to heat the gas sensitive element 3 which was the film of γ-$Fe_2O_3$. The gold electrodes 2 of the forsterite tube were connected to an electrometer to measure the electrical resistance of the gas sensitive element which was the film of γ-$Fe_2O_3$. Dried air was flowed into the measuring chamber at a flow rate of 1.7 liters per minute. The electrical resistance of the gas sensitive element was 10.5 MΩ at room temperature. As the electrical voltage on the platinum wire 4 was increased, the temperature of the gas sensitive element was increased up to 270° C. The electrical resistance of the gas sensitive element was 1.2MΩ at 270° C. The gas which was flowing into the measuring chamber was then changed by the bulb to air containing one percent by volume propane, which was flowed into the measuring chamber at a flow rate of 1.7 liters per minute. The electrical resistance of the gas sensitive element was rapidly changed to 115kΩ with the change of the gas. The above results showed that the sensitivity ($R_A/R_G$) of the reducing gas sensor was 10.4. The same tests of the reducing gas sensor were repeated a day, a week and a month after the gas sensor preparation, but the values of the electrical resistances in air and in air containing one percent by volume propane at 270° C fell within the deviation limits of ± 5 percent.

EXAMPLE II

Figure 2:
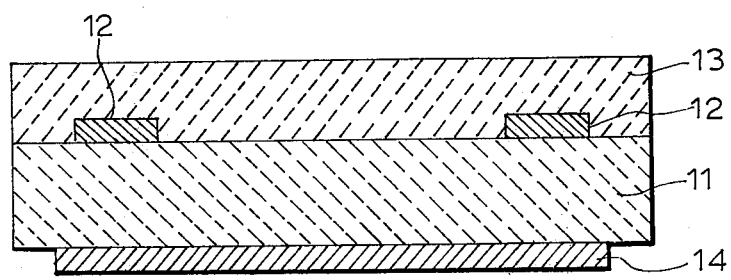
FIG. 2 is a cross-sectional view of another example of a reducing gas sensor contemplated by this invention.

Five hundred grams of lepidocrocite (γ-FeOOH) powder and one liter of distilled water were mixed in a ball mill for one hour to produce a homogeneous slurry. Referring to FIG. 2, the homogeneous slurry was applied to an alumina plate 11 which was 30mm in length, 12mm in width and 1mm thick. The alumina plate had a pair of comb-like gold electrodes 12 deposited thereon. The gap between the electrodes was 0.5mm. The alumina plate with the slurry as a film on the central portion was dried at room temperature for 30 minutes and then fired at 400° C for 30 minutes in air. Thereby, the film of γ-FeOOH was transformed to a film of γ-$Fe_2O_3$ 20 microns thick, which film was a gas sensitive element 13. A heater element 14 of platinum foil was placed in contact with the other surface of the alumina plate as shown in FIG. 2. The thus produced reducing gas sensor was placed in the measuring chamber, which was a glass tube 40mm in inner diameter and 100mm in length, and the same measuring procedures as in Example I were carried out for the thus made reducing gas sensor. The electrical resistances of the gas sensitive element were 970kΩ at 270° C in air and 8.64kΩ at 270° C in air containing one percent by volume propane. The sensitivity of the reducing gas sensor was 112. Air without propane was again flowed into the measuring chamber for 20 minutes. The electrical resistance of the reducing gas sensor returned to 945kΩ. Again the air containing one percent by volume of propane was flowed into the chamber, and the electrical resistance of the reducing gas sensor became 8.61kΩ. The measuring procedures were repeated. The electrical resistances in air were in the range of 975 to 878kΩ, but the electrical resistances in air containing one percent by volume propane was just 8.6kΩ and did not deviate from that 8.6kΩ.

Figure 3:
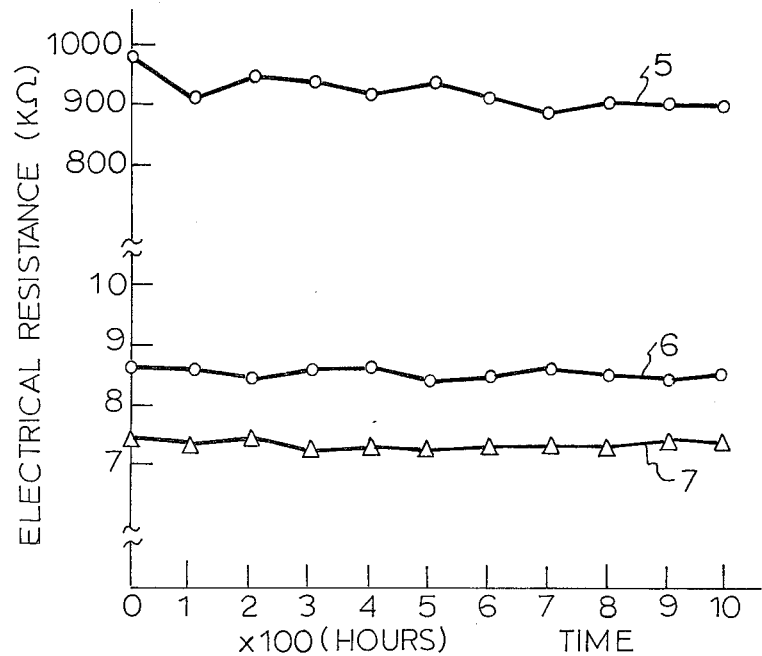
FIG. 3 is a graph showing the relation between the electrical resistances of the reducing gas sensor according to FIG. 2 kept at 270° C in three different atmospheres and the time during which the sensor is kept therein.

FIG. 3 shows the electrical resistances at 270° C of the thus made reducing gas sensor in air (curve 5), in air containing one percent by volume propane (curve 6) and in air containing one percent by volume city gas (curve 7) measured at various times (100 hour intervals) up to 1000 hours during which the sensor was kept in the respective atmospheres. The electrical resistances fell within the deviation limits of ± 3 percent in air and ± 10 percent in air containing one percent by volume propane.

EXAMPLE III

Five hundred grams of magnetite ($Fe_3O_4$) powder and one liter of distilled water were mixed in a ball mill for one hour to produce a homogeneous slurry. The homogeneous slurry was applied to an alumina plate just as in example II. Eight plates of alumina each having the slurry thereon in a film were dried at room temperature for 30 minutes and then fired at eight different temperatures, respectively, between 100° and 600° C for 30 minutes in air. A heater element was placed on each plate in the same manner as in Example II. The thus produced reducing gas sensors were placed in the measuring chamber. The same measuring procedures were carried out for the reducing gas sensors.

Figure 4:
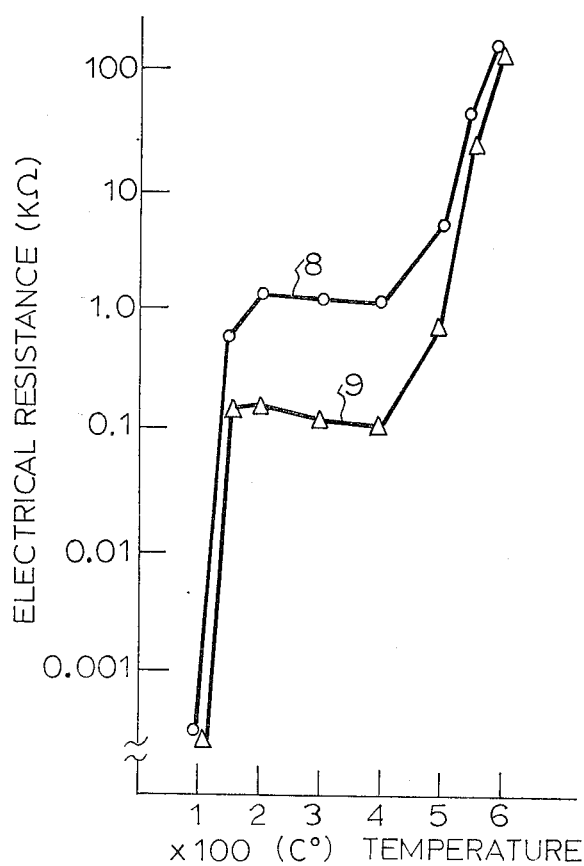
FIG. 4 is a graph showing the relation between the electrical resistances of reducing gas sensors like those of FIG. 2 kept at 270° C in two different atmospheres and the temperatures at which firing is carried out for making the gas sensitive elements.

FIG. 4 shows the electrical resistances at 270° C of the thus made reducing gas sensors in air (curve 8) and in air containing one percent by volume propane (curve 9).

EXAMPLE IV

A reducing gas sensor was produced in the same manner as in Example III. The alumina plate with the slurry forming the film was fired at 400° C for 30 minutes in air. The thus produced reducing gas sensor was placed in the measuring chamber the same as used in Example I and the electrical resistance measured. The electrical resistances of the reducing gas sensor were 1.35MΩ in air and 11.5kΩ in air containing one percent by volume propane at 270° C.

Figure 5:
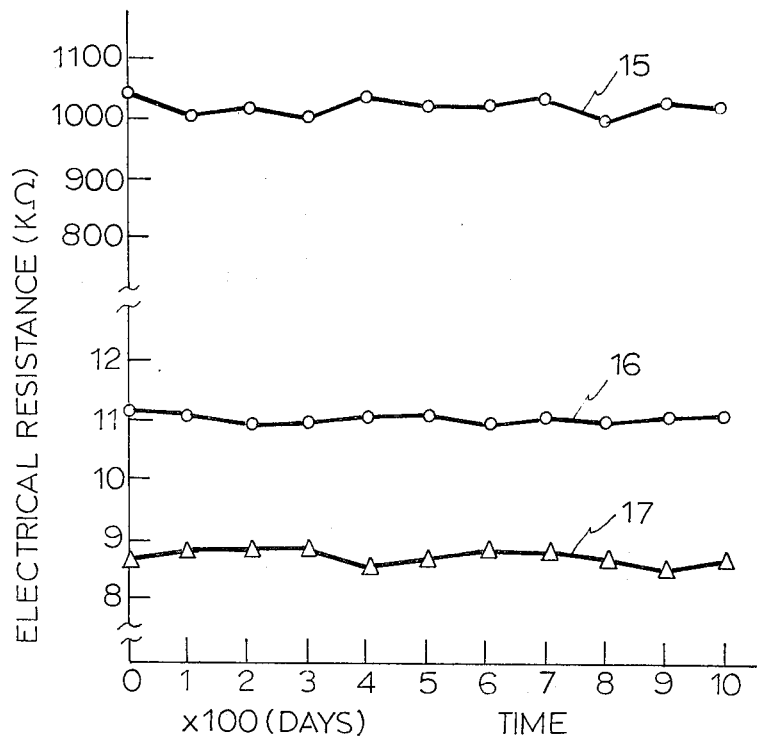
FIG. 5 is a graph showing the relation between the electrical resistances of a reducing gas sensor according to FIG. 2 kept at 270° C in three different atmospheres and the time during which the sensor is kept therein.

FIG. 5 shows the electrical resistances of the reducing gas sensor at 270° C in air (curve 15), in air containing one percent by volume propane (curve 16), and in air containing one percent by volume city gas (curve 17) measured at various times (100 hour intervals) up to 1000 hours during which the sensor was kept in the respective atmospheres.

Figure 6:
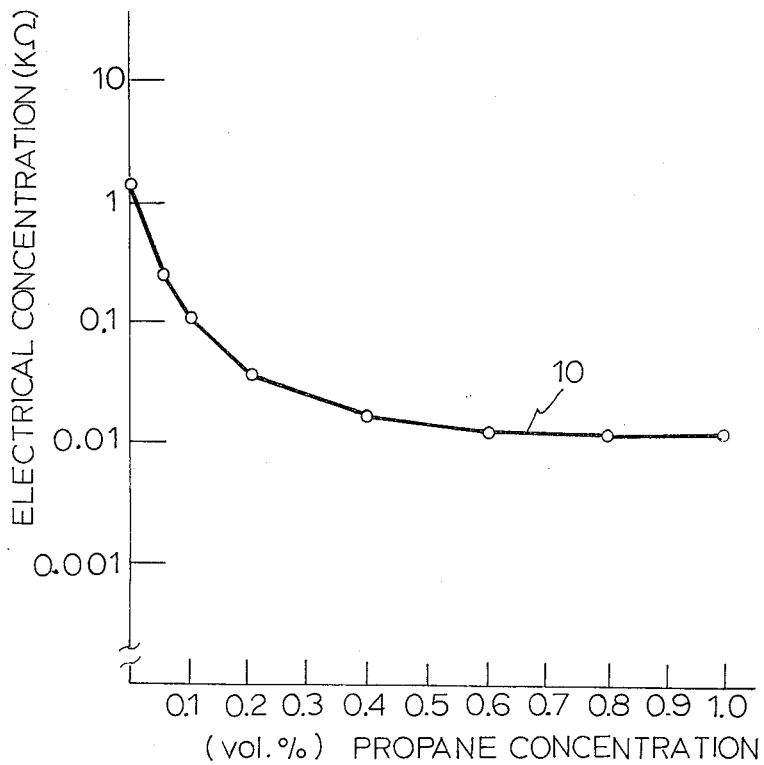
FIG. 6 is a graph showing the relation between the electrical resistances of a reducing gas sensor according to FIG. 2 kept at 270° C in an air base atmosphere and the amount of propane gas contained in the air base atmosphere.

Then, the electrical resistances of the reducing gas sensor in air containing various amounts of propane were measured at 270° C. FIG. 6 shows the electrical resistances (curve 10) in air containing 0, 0.05, 0.1, 0.2, 0.4, 0.6, 0.8 and 1.0 percent by volume propane, respectively.

EXAMPLE V

Figure 7:
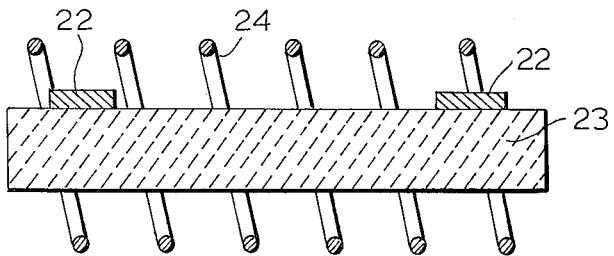
FIG. 7 is a cross-sectional view of still another example of a reducing gas sensor contemplated by this invention.

Magnetite ($Fe_3O_4$) powder which had an average particle size of 0.2 micron was compressed into a plate 13mm square and 2mm thick at a pressure of 1000kg/cm². The compressed magnetite plate was fired at 950° C for two hours in nitrogen gas. Referring to FIG. 7, the fired plate 23 was then fired at 450° C for one hour in air. A pair of comb-like gold electrodes 22 were formed on the fired plate by vacuum evaporation. A heater element 24 was placed nearby the fired plate. The thus produced reducing gas sensor was placed in the measuring chamber the same as in Example I. The electrical resistances of the reducing gas sensor were 5.5MΩ at room temperature, 120kΩ in air and 4.0kΩ in air containing 0.1 percent by volume propane at 270° C. The sensitivity of the reducing gas sensor was 30.

EXAMPLE VI

Alpha ferric oxide powder which had a particle size of 0.1 micron and a solution of 2 percent polyvinyl alcohol were mixed in a mortar to produce a homogeneous paste. The homogeneous paste was applied as a film of 0.1 mm thickness onto an alumina plate which had a length of 30 mm, a width of 10 mm and a thickness of 1 mm. The alumina plate had a pair of comb-like platinum electrodes deposited thereon. The gap between the electrodes was 0.5 mm. The film of α-ferric oxide applied to the alumina plate was dried at 60° C for 3 hours and then at 100° C for an hour. The dried film was prefired at 1100° C for 6 hours in oxygen. The electrical resistivity of the prefired film was $10^8$ Ω-cm, and the film was still in the α-$Fe_2O_3$ crystal phase. The prefired film was fired at 450° C for 1 hour in hydrogen gas saturated with water vapor. The reduced film was further fired at 350° C for 2 hours in air. A heater element of platinum foil was placed in contact with the other surface of the alumina plate. The thus produced reducing gas sensor had the resistance measured by the same procedures as in Example I. The electrical resistances of the reducing gas sensor were 350 kΩ in air and 6.2 kΩ in air containing 1 percent by volume propane at 270° C.

Figure 8:
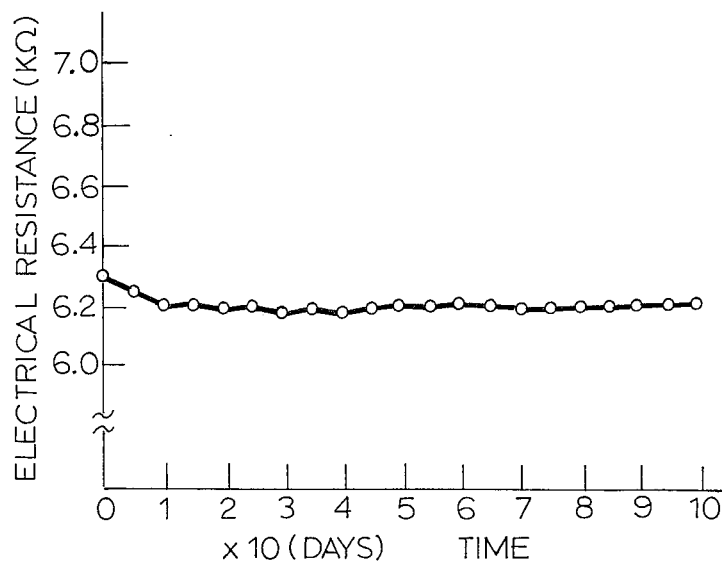
FIG. 8 is a graph showing the relation between the electrical resistances of a reducing gas sensor according to FIG. 2 kept at 270° C in air containing 1 percent by volume propane gas and the time during which the sensor is kept therein.

FIG. 8 shows the electrical resistances of the reducing gas sensor in air containing 1 percent by volume propane repeatedly measured at 270° C at various times (5 day intervals) up to 100 days during which the gas sensor was kept in the atmosphere.

EXAMPLE VII

Figure 9:
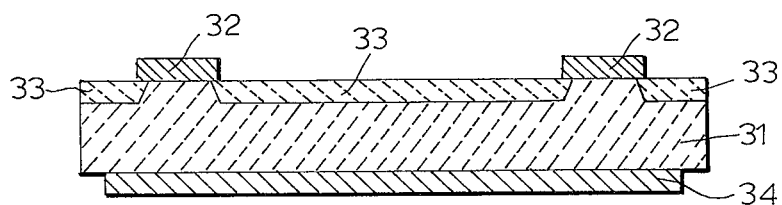
FIG. 9 is a cross-sectional view of yet another example of a reducing gas sensor contemplated by this invention.

A solution of 1 percent polyvinyl alcohol was added to α-$Fe_2O_3$ powder in a ratio of 0.1 ml of the solution and one gram of the α-$Fe_2O_3$ powder. The α-$Fe_2O_3$ powder with the polyvinyl alcohol solution was compressed to a plate 50 mm in length, 20 mm in width and mm thick. The plate was fired at 1000° C for 3 hours in an oxygen atmosphere. The fired plate was sliced into a plate 20 mm in length, 10 mm in width and·1 mm thick. Referring to FIG. 9, silver electrodes 32 were deposited on the surface of the sliced plate 31 in the form of a pair of comb-like electrodes with the gap between the electrodes being 0.5 mm just as in Example VI. The sliced plate was reduced by firing at 350° C for 15 minutes in hydrogen gas saturated with water vapor. The reduced plate was further fired at 350° C for 2 hours in air. The surface layer 33 of the further fired plate was transformed to γ-$Fe_2O_3$ to a depth of about 10 microns. The center part 31 of the further fired plate was still sintered α-ferric oxide. The surfaces of the further fired plate except the surface which had the silver electrodes thereon were cut off to a depth of 100 microns. A heater element 34 of platinum foil was placed in contact with the other cut surface of the fired plate. The thus produced reducing gas sensor was tested by the same procedures as in Example 1. The electrical resistance of the reducing gas sensor was 290 k Ω at 270° C in air.

Figure 10:
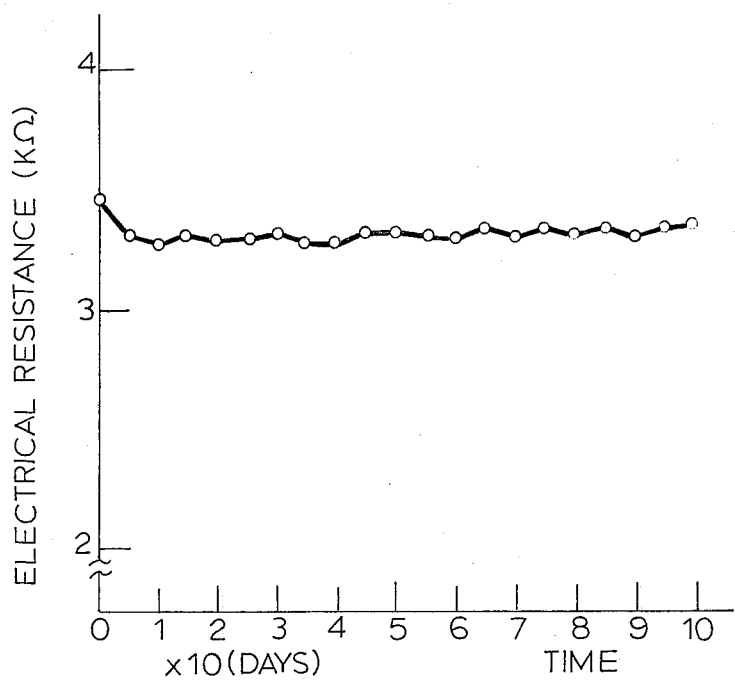
FIG. 10 is a graph showing the relation between the electrical resistances of a reducing gas sensor according to FIG. 9 kept at 270° C in air containing 1 percent by volume of propane gas and the time during which the sensor is kept therein.

FIG. 10 shows the electrical resistances of the reducing gas sensor in air containing 1 percent by volume propane repeatedly measured at 270° C at various times (5 day intervals) up to 100 days during which the sensor was kept in the atmosphere.

What is claimed is:

1. A reducing gas sensor comprising a gas sensitive element composed mainly of γ-ferric oxide ($\gamma$-$Fe_2O_3$), a pair of electrodes on said sensitive element, and a heater element adjacent said elements, whereby when said gas sensitive element is heated to an elevated temperature it undergoes a rapid decrease in electrical resistance upon coming in contact with an atmosphere containing a reducing gas.

2. A reducing gas sensor according to claim 1, wherein said gas sensitive element is composed of a sintered body of γ-ferric oxide.

3. A reducing gas sensor according to claim 2, wherein said gas sensitive element is in the form of a sintered plate of γ-ferric oxide.

4. A reducing gas sensor according to claim 2, wherein said gas sensitive element is in the form of a sintered film of γ-ferric oxide on an insulator substrate.

5. A reducing gas sensor according to claim 2, wherein said gas sensitive element is in the of a thin surface layer of γ-ferric oxide formed on a sintered plate of α-ferric oxide.

6. A method of producing a reducing gas sensor, comprising firing an iron oxide at a temperature between 100° C and 600° C for 30 minutes to 5 hours in an oxidizing atmosphere to obtain a sintered γ-ferric oxide ($\gamma$-$Fe_2O_3$) as a gas sensitive element, applying a pair of electrodes to said gas sensitive element and placing a heater element near said gas sensitive element.

7. A method of producing a reducing gas sensor according to claim 6, wherein said sintered γ-ferric oxide is obtained by mixing γ-ferric oxide powder and water to prepare a homogeneous mixture, applying said mixture to an insulator substrate to form thereon a thin film of said mixture, and firing said thin film at a temperature between 350° C and 600° C for 30 minutes to 5 hours in an oxidizing atmosphere.

8. A method of producing a reducing gas sensor according to claim 6, wherein said sintered γ-ferric oxide is obtained by mixing powdered lepidocrocite ($\gamma$-FeOOH) and water to prepare a homogeneous mixture, applying said mixture to an insulator substrate to form thereon a thin film of said mixture, and firing said thin film at a temperature between 150° C and 600° C for 30 minutes to 5 hours in an oxidizing atmosphere.

9. A method of producing a reducing gas sensor according to claim 6, wherein said sintered γ-ferric oxide is obtained by mixing powdered magnetite ($\gamma$-$Fe_3O_4$) and water to prepare a homogeneous mixture, applying said mixture to an insulator substrate to form thereon a thin film of said mixture, and firing said thin film at a temperature between 100° C and 600° C for 30 minutes to 5 hours in an oxidizing atmosphere.

10. A method of producing a reducing gas sensor according to claim 6, wherein said sintered γ-ferric oxide is obtained by pressing magnetite powder to prepare a plate of said magnetite, prefiring said plate at a temperature between 600° and 1100° C for 30 minutes to 10 hours in a non-oxidizing atmosphere, and firing said prefired plate of magnetite at a temperature between 100° and 600° C for 30 minutes to 5 hours in an oxidizing atmosphere.

11. A method of producing a reducing gas sensor according to claim 6, wherein said sintered γ-ferric oxide is obtained by mixing α-ferric oxide powder and polyvinyl alcohol solution to prepare a homogeneous mixture, appyling said mixture to an insulator substrate to form thereon a thin film of said mixture, prefiring said thin film at a temperature between 700° and 1300° C for 1 to 10 hours in an oxidizing atmosphere, firing said prefired film at a temperature between 200° and 450° C for 15 minutes to 3 hours in hydrogen gas saturated with water vapor, and further firing the thus fired film at a temperature between 100° C and 600° C for 1 to 5 hours in an oxidizing atmosphere.

12. A method of producing a reducing gas sensor according to claim 6, wherein said sintered γ-ferric oxide is obtained by pressing α-ferric oxide powder to prepare a plate of said α-ferric oxide, prefiring said plate at a temperature between 800° and 1000° C for 1 to 3 hours in an oxidizing atmosphere, firing and prefired plate at a temperature between 200° and 450° C for 10 minutes to 2 hours in hydrogen gas saturated with water vapor, and further firing the thus fired plate at a temperature between 100° and 600° C for 30 minutes to 3 hours in an oxidizing atmosphere so as to transform the thin surface layer of said further fired plate to γ-ferric oxide.

* * * * *

UNITED STATES PATENT AND TRADEMARK OFFICE
CERTIFICATE OF CORRECTION

PATENT NO. : 3,999,947
DATED : December 28, 1976
INVENTOR(S) : Toshihiro Mihara and Masatake Ayusawa It is certified that error appears in the above-identified patent and that said Letters Patent are hereby corrected as shown below:

Fig. 5, last line, change "DAYS" to -- HOURS --.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks